United States Patent [19]
Galey et al.

[11] Patent Number: 5,709,848
[45] Date of Patent: Jan. 20, 1998

[54] PHOTOCLEAVABLE METAL-CHELATING AGENTS AND COMPOSITIONS CONTAINING THE SAME

[75] Inventors: Jean-Baptiste Galey, Aulnay-sous-Bois; Jacqueline Dumats, Villepinte, both of France

[73] Assignee: L'Oreal, Paris, France

[21] Appl. No.: 528,653

[22] Filed: Sep. 7, 1995

[30] Foreign Application Priority Data

Sep. 8, 1994 [FR] France ................... 94 10763

[51] Int. Cl.$^6$ .................................. A61K 7/42
[52] U.S. Cl. ................ 424/59; 424/60; 424/70.1; 424/400; 424/401
[58] Field of Search ................ 424/59, 60, 400, 424/401, 70.1

[56] References Cited

FOREIGN PATENT DOCUMENTS

A-0 313 305  4/1989  European Pat. Off. .
A-2 698 095  5/1994  France .
A-36 32 329  3/1988  Germany .

OTHER PUBLICATIONS

Vaverkova et al, CA 97: 018948c 1982.

*Primary Examiner*—Shelley A. Dodson
*Attorney, Agent, or Firm*—Oblon, Spivak, McClelland, Maier & Neustadt, P.C.

[57] ABSTRACT

Chelating agents for a transition metal, which exhibit the special feature of being photocleavable, that is containing a chelating functional group blocked by a photocleavable protecting group such that the chelating functional group is released only on exposure to luminous, specially ultraviolet, radiation, trap the transition metals released by the action of the luminous radiation, without exhibiting the side effects observed with conventional chelating agents. Compositions, especially cosmetic and/or dermatological ones, containing at least one such chelating agent are useful for protecting the skin, the mucosa, and/or the hair against ultraviolet radiation.

15 Claims, No Drawings

PHOTOCLEAVABLE METAL-CHELATING AGENTS AND COMPOSITIONS CONTAINING THE SAME

BACKGROUND OF THE INVENTION

1. Field of the Invention

The present invention relates to new chelating agents for a transition metal and to compositions, especially cosmetic and/or dermatological and/or hygienic compositions, containing at least one such chelating agent. These compositions are useful in particular for protecting the skin, the hair and/or the mucosa against the effects induced by luminous, especially ultraviolet, radiation, and for preventing and/or combating cutaneous photoaging. Thus, the present invention further relates to methods for protecting the skin, the hair, and/or the mucosa from the damaging effects of light, especially ultraviolet light, and for preventing and/or combating cutaneous photoaging.

2. Discussion of the Background

It is known that activated oxygen species (singlet oxygen, superoxide anion, aqueous hydrogen peroxide and the hydroxyl radical) take part in the process of photoaging and there are numerous works on the subject (see, for example, P. Morliére et al., *Path. Biol.*, vol. 40 (2), p. 160–168 (1992)). It is also known that transition metals, and in particular iron and copper, play an essential part in the molecular reactions taking place in tissues when they are exposed to the luminous radiation. These reactions create damage called "oxidative damage" which results in a premature aging of the skin (see, for example, C. W. Trenam et al., *J. Invest. Dermatol.*, vol. 99, p.675–682 (1992) and T. P. Ryan et al., *Critical Reviews in Toxicology*, vol. 22 (1), p. 119–141 (1992)).

Furthermore, iron and, to a lesser extent, copper are elements which are essential to life and which play a determining part in many biological phenomena. These elements are present in a number of places in living tissues and chiefly within the active sites of metalloenzymes, or else stored in reserve or transport proteins. Iron is involved especially in oxygen transport, storage and activation (see M. Fontecave et al., *Bull. Soc. Chim.*, vol. 130, p.77–85 (1993)).

In a normal situation, these metals, and iron in particular, are never in a free or available form and cannot therefore catalyse the redox reactions resulting in oxidative damage. On the other hand, in an "oxidative stress" situation, in particular during exposure to luminous radiation, small quantities of metals can be released and thus become available for catalysing these reactions. In particular, it has been observed that ferritin releases iron under the action of ultraviolet rays (see M. Aubailly et al., *Photochem. Photobiol.*, vol. 54(5), p.769–773 (1991)).

To avoid this phenomenon it is known to employ chelating agents for transition metals and especially chelating agents for iron which, by trapping the iron, inhibit the oxidative processes to which it could give rise. Thus, EP-A-313305, EP-A-496433, and EP-A-496434 describe photoprotective compositions employed in topical application which include chelating agents which trap free iron and which are intended to prevent damage to the skin caused by exposure to ultraviolet rays.

Nevertheless, these chelating agents have side effects, and especially risks of chronic toxicity, and these risks restrict their use as agents for skin protection. These chelating agents can, in fact, interfere with the metabolism of iron which, because of its vital role in the functioning of the cells in the human body, must be preserved and, in particular, they can block iron, even that necessary for the functioning of the tissues. Attempts are consequently made to avoid, or at least to limit, the use of these chelating agents for any substance that must be in contact with living tissue.

Thus, there is a continuing need for chelating agents for transition metals, which prevent the damage caused by these metals, and especially iron and copper, during exposure to luminous, and especially ultraviolet, radiation, without exhibiting the disadvantages of the chelating agents usually employed for trapping these metals.

Quinoline derivatives containing nitro groups are known. They are used as synthetic intermediates (see DE-A-3632329) and as chamomille growth biostimulators (see Chemical Abstract, vol. 97, n°3, 018948).

SUMMARY OF THE INVENTION

Accordingly, it is one object of the present invention to provide novel compositions which protect the skin, hair, and/or mucosa from the damaging effects of luminous, especially ultraviolet, radiation.

It is another object of the present invention to provide novel compositions for combating cutaneous photoaging.

It is another object of the present invention to provide novel compositions which prevent the damage caused by transition metals, especially iron and copper, during exposure to luminous, especially ultraviolet, radiation.

It is another object of the present invention to provide novel compositions which prevent the damage caused by transition metals, especially iron and copper, during exposure to luminous, especially ultraviolet, radiation, without interfering with the normal function of such metals.

It is another object of the present invention to provide a novel method for protecting the skin, hair, and/or mucosa from the damaging effects of luminous, especially ultraviolet, radiation.

It is another object of the present invention to provide a novel method for combating cutaneous photoaging.

It is another object of the present invention to provide a novel method for preventing the damage caused by transition metals, especially iron and copper, during exposure to luminous, especially ultraviolet, radiation.

It is another object of the present invention to provide a novel method for preventing the damage caused by transition metals, especially iron and copper, during exposure to luminous, especially ultraviolet, radiation, without interfering with the normal function of such metals.

These and other objects, which will become apparent during the following detailed description, have been achieved by the inventors' discovery that compositions which contain a chelating agent which acquires the ability to chelate only upon exposure to ultraviolet light are effective for realizing the above objects.

DETAILED DESCRIPTION OF THE PREFERRED EMBODIMENTS

The chelating agents for transition metals of the present invention exhibit the special feature of acquiring their chelating property only when exposed to ultraviolet radiation, that is to say only when it is necessary to neutralize the traces of the metals intervening in the oxidative damage phenomena. The chelating agents of the invention therefore make it possible to limit the side effects observed with conventional chelating agents. The present invention therefore relates to the use, as a chelating agent for a transition metal, of a compound containing a group containing at least one chelating functional group for a transition metal, blocked by at least one photocleavable substituent.

The transition metals to which the invention applies are the metals which have an atomic number included in the range running from 21 to 30, and are, more particularly, iron and copper.

The chelating agents for transition metals according to the present invention have at least one chelating functional group blocked by a substituent which has the special feature of separating itself from the chelating functional group(s) during exposure to luminous radiation and thus exposing the chelating functional group(s) which will be capable of playing their part as chelating agent. Consequently, when they are not exposed to luminous radiation, the chelating agents of the invention have a very low, or even nil, affinity for iron or copper and cannot therefore cause any detrimental side effects on the metabolism of iron and/or copper. On the other hand, when exposed to luminous radiation, they expose the chelating functional group(s) which have a high affinity for transition metals and will trap the metal released, thus preventing damage to the tissues.

Thus, in another embodiment, the present invention provides compositions which include a chelating agent for a transition metal, characterized in that the chelating agent contains a group containing at least one chelating functional group for a transition metal, blocked by a photocleavable substituent and a cosmetically and/or dermatologically acceptable medium.

In another embodiment, the present invention provides compositions for protecting the skin, the hair and more especially the scalp, and/or the mucosa, against the effects induced by luminous radiation and for preventing and/or combating cutaneous photoaging, which contain a chelating agent for a transition metal, characterized in that the chelating agent contains a group containing at least one chelating functional group for a transition metal blocked by a photocleavable substituent and a cosmetically and/or dermatologically acceptable medium.

In another embodiment, the present invention provides the use of a chelating agent for a transition metal, containing a group containing at least one chelating functional group blocked by at least one photocleavable substituent, in a cosmetic and/or dermatological composition for protecting the skin, the hair and/or the mucosa against the effects induced by luminous radiation and/or for preventing and/or combating cutaneous photoaging.

In a further embodiment, the present invention provides compositions as defined in the form of a dermatological salve and/or ointment which are intended to protect the skin, the hair and/or the mucosa against the effects induced by luminous radiation and/or for preventing and/or combating cutaneous photoaging.

In another embodiment, the present invention provides a method for the cosmetic treatment of the skin, hair and/or mucosa by applying the composition as defined above to the skin, the hair and/or the mucosa.

The chelating functional group of the chelating agent according to the present invention may be any chelating functional group for transition metals and especially an amine, carbonyl, nitrile, oxime, carboxylic, hydroxyl, hydroxamic, alkoxy, enolic, phenolic, phenoxy, hydrazide or sulphur-containing functional group and combinations thereof.

Chelating groups containing one or more of these functional groups which may be mentioned are, for example, aromatic or aliphatic amines, aliphatic or aromatic ketones, aliphatic or aromatic aldehydes, dioximes and ketoximes, aliphatic or aromatic carboxylic acids and their esters and their salts, phenols and their derivatives, aliphatic or aromatic carboxylic hydroxyacids, hydrazides, catecholates, ketoenolates, hydroxamates and aromatic hydroxyamines.

Chelating groups containing several of these functional groups which may be mentioned in particular are hydroxypyridinones, dicarboxylic amines, o-hydroxybenzylamines and hydroxamates.

The following chelating groups may be specifically: the hydroxypyridinones of the formula:

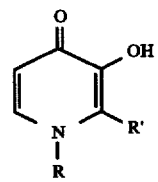

where R and R' denote, independently of each other, an alkyl, especially methyl, residue;
the aminocarboxylate derivatives of the formula:

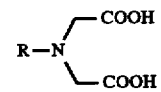

where R denotes an alkyl residue optionally carrying another aminocarboxylate functional group. It may be, for example, diethylenetriaminepentaacetic acid (DTPA);
the o-hydroxybenzylamine derivatives of the formula:

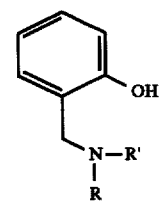

where R and R' denote, independently of each other, an acetic or alkyl residue optionally carrying another chelating functional group. It may be, for example, N,N'-bis(2-hydroxybenzyl)ethylenediaminediacetic acid;
the hydroxamate derivatives of the formula:

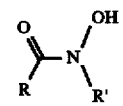

where R and R' denote, independently of each other, an aminoacid chain, optionally carrying another hydroxamate functional group. It may be, for example, desferioxamine B.

The blocking of the chelating functional groups may be carried out with photocleavable protecting groups conventionally employed in synthetic chemistry, these groups varying according to the nature of the chelating functional group to be blocked.

They are especially p-methoxyphenacyl, 2-nitrobenzyl, 2-nitrobenzyloxycarbonyl, 2-nitrophenylethylene glycol, benzyloxycarbonyl, 3,5-dimethoxybenzyloxycarbonyl, α,α-dimethyl-3,5-dimethoxybenzyloxycarbonyl, 3-nitrophenyl, 3-nitrophenoxy, 3,5-dinitrophenoxy, 3-nitrophenoxycarbonyl, phenacyl, 4-methoxyphenacyl, α-methylphenacyl, 3,5-dimethoxybenzoinyl and 2,4-dinitrobenzenesulphenyl groups.

The chelating agent according to the invention may be, for example, a compound which, by photocleavage, will give rise to the formation of an aromatic amine, an amine, a phenol, a carbonyl compound, or an alcohol.

Aromatic amine N-oxides may be mentioned, for example, as compounds yielding an aromatic amine by photocleavage.

Examples which may be mentioned of compounds which yield an amine by photocleavage are aryl formamides, benzyl carbamates, benzylsulphonamides, toluenesulphonamides, 3,5-dimethoxybenzyl carbamates, 3,4-dimethoxy-6-nitrobenzyl carbamates, 1-methyl-1-(3,5-dimethoxyphenyl)ethyl carbamates, N-o-nitrobenzylamines, o-nitrobenzyl carbamates and m-nitrophenyl carbamates.

Examples which may be mentioned of compounds yielding a carboxylic acid by photocleavage are bis(o-nitrophenyl)methyl esters, α-(3,5-dimethoxyphenyl) phenacyl esters, 2,4-dinitrophenylsulphenyl esters, 2-(9,10-dioxo)anthrylmethyl esters, p-methoxyphenacyl esters, α-methylphenacyl esters, nitroamides, o-nitroanilides, o-nitrobenzyl esters, N-7-nitroindolylamides and N-8-nitro-1,2,3,4-tetrahydroquinolylamides.

Examples which may be mentioned of compounds yielding a phenol by photocleavage are 9-fluorenecarboxylic esters, o-nitrobenzyl ethers and xanthenecarboxylic esters.

Examples which may be mentioned of compounds yielding a carbonyl compound by photocleavage are S,S-dibenzylacetals, N,N-dimethylhydrazones, 1,3-dithiolanes and 1,3-oxathiolanes.

Examples which may be mentioned of compounds yielding an alcohol by photocleavage are nitrates, o-nitrobenzyl carbonates and o-nitrobenzyl ethers.

The photocleavable protecting groups preferably employed in the invention are, in particular:

p-methoxyphenacyl esters, which protect carboxylic chelating functional groups and whose photocleavage reaction under UV is the following:

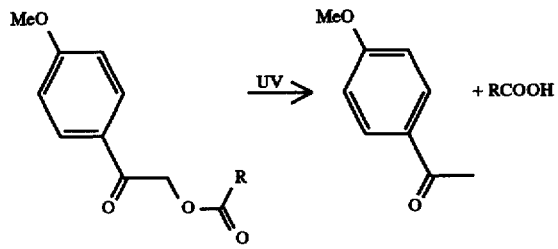

where RCOOH denotes the chelating compound which no longer contains any protecting group and is therefore capable of trapping the transition metals;

o-nitrobenzyl ethers, which protect phenol chelating functional groups, whose photocleavage reaction under UV is the following:

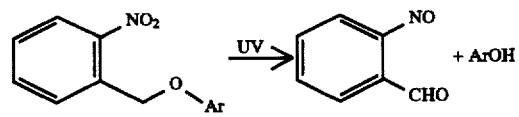

where ArOH denotes the chelating compound which no longer contains any protecting group and is therefore capable of trapping transition metals.

More particularly, the preferred photocleavable chelating agents of the invention have the following formulae:

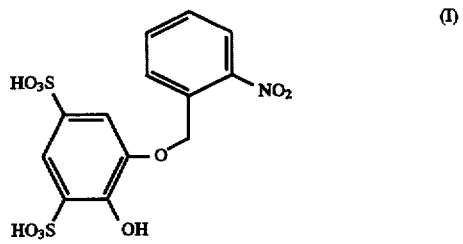

2-(o-nitrobenzyloxy)-phenol-4,6-disulfonic acid

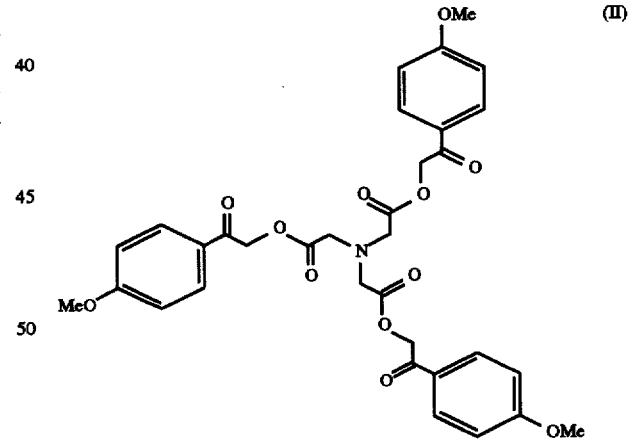

p-methoxyphenacyl tetraester of nitrilotriacetic acid

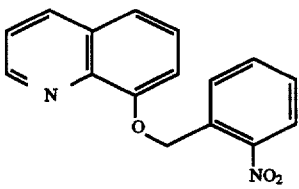

8-(2-nitrobenzyloxy)quinoline                                                  (III)

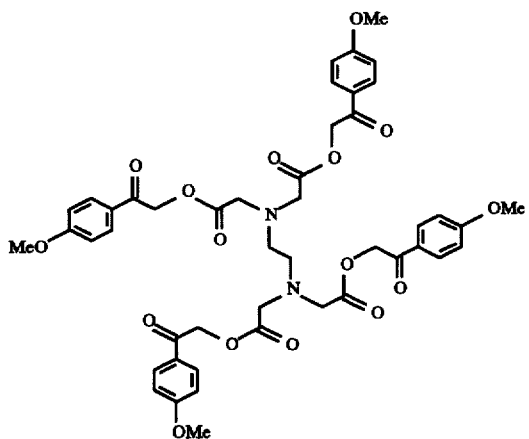

p-methoxyphenacyl tetraester of ethylenediaminetetraacetic acid                (IV)

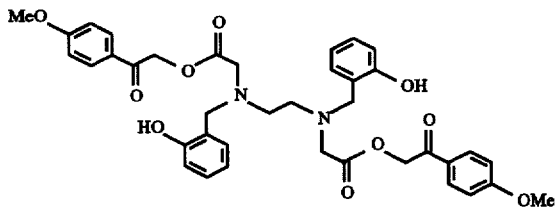

p-methoxyphenacyl diester of N,N'-bis(2-hydroxybenzyl) ethylenediaminediacetic acid    (V)

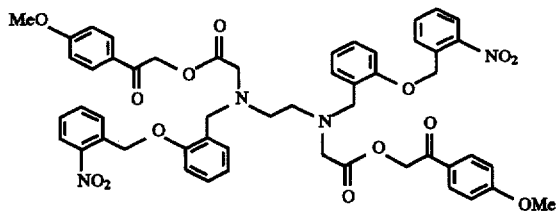

p-methoxyphenacyl diester of N,N'-bis[2-(o-nitrobenzyloxy)phenyl]ethylenediaminediacetic acid    (VI)

The chelating agent according to the present invention may advantageously be employed in the present cosmetic and/or dermatological compositions at a concentration ranging from 0.001% to 10% by weight, preferably from 0.05% to 5% by weight, based on the total weight of the composition.

The compositions according to the present invention contain a cosmetically and/or dermatologically acceptable medium, that is a medium which is compatible with the skin. They may be presented in any of the galenic forms normally employed for a topical application, which are intended particularly for the cosmetic and/or dermatological fields. In particular, the compositions may be presented in the form of aqueous, alcoholic or hydroalcoholic solutions, in the form of creams, of hydrophilic or lipophilic gels, of water-in-oil or oil-in-water emulsions, of creams or gels capable of foaming, or aerosol compositions, or else in the form of microgranulates, of powders or of vesicular dispersions of ionic and/or nonionic type. These compositions are prepared using the methods which are conventional in the fields in question.

The quantities of the various constituents of the compositions according to the present invention are those conventionally employed in the fields of cosmetics or dermatology or hygiene.

The present compositions constitute especially cleansing, protecting, treatment or care compositions for the face, for the neck, for the hands or for the body (for example day creams, creams for makeup removal, sun creams or oils, cleansing milks, milks for makeup removal, body milks), makeup compositions (for example foundations), and artificial tanning compositions.

The present chelating agents may also be employed in various compositions for hair, and especially treating lotions, styling creams or gels, dye compositions, lotions or gels for counteracting hair loss.

When the composition of the present invention is an emulsion, the proportion of fatty substance may range from 5% to 80% by weight, preferably from 5% to 50% by weight, based the total weight of the composition. The fatty substances and the emulsifiers employed in the composition in the form of emulsion are chosen from those conventionally employed in the field of cosmetics or dermatology. The emulsifiers may be present in the composition in a proportion ranging from 0.3% to 30% by weight, preferably from 0.5 to 30% by weight, based the total weight of the composition. The composition may additionally contain lipid vesicles.

In a known manner, the cosmetic or dermatological composition of the present invention may also contain adjuvants which are usual in the field of cosmetics or dermatology, such as hydrophilic or lipophilic gelling agents, hydrophilic or lipophilic active substances, stabilizers, antioxidants, solvents (alcohols), perfumes, fillers, screening agents and colorants. The quantities of these various adjuvants are those conventionally employed in the fields in question and, for example, from 0.01% to 20% by weight, based the total weight of the composition. Depending on their nature, these adjuvants may be introduced into the fatty phase, into the aqueous phase and/or into the lipid vesicles.

Fatty substances which may be mentioned as being usable in the compositions of the present invention are mineral oils, vegetable oils (jojoba oil) and their hydrogenated derivatives, animal oils (lanolin), synthetic oils (isopropyl myristate), silicone oils (cyclopentadimethylsiloxane), and fluorinated oils. Other fatty substances such as fatty alcohols (cetyl alcohol, stearyl alcohol), fatty acids (stearic acid) and waxes may be added to these oils.

Examples of hydrophilic gelling agents which may be mentioned are carboxyvinyl (carbomer) polymers, acrylic copolymers, polyacrylamides, polysaccharides, natural gums, and clays, and lipophilic gelling agents which may be mentioned are modified clays and metal salts of fatty acids.

Examples of active substances which may be mentioned are proteins or protein hydrolysates, amino acids, polyols, sugars and sugar derivatives, vitamins, hydroxyacids, ceramides, essential oils, and salicylic acid and its derivatives.

Other features of the invention will become apparent in the course of the following descriptions of exemplary embodiments which are given for illustration of the invention and are not intended to be limiting thereof.

EXAMPLES

Example 1

Preparation of the p-methoxyphenacyl triester of nitrilotriacetic acid (compound of formula II).

1 g of nitrilotriacetic acid is dissolved in 15 ml of dimethylformamide containing 2.3 ml of triethylamine. The mixture is cooled to 0° C., and then 3.6 g of 2-bromo-4'-methoxyacetophenone in solution in 20 ml of dimethylformamide (DMF) are added to it. The mixture is kept at 0° C. for 24 hours. The mixture is then poured onto 150 g of ice, and an extraction is carried out three times into 50 ml of dichloromethane. The organic phase is washed with water, dried over sodium sulfate, and then evaporated to dryness. The oily product obtained is purified by passing through a silica column with a dichloromethane/methanol (95:5) mixture as eluent.

0.8 g of p-methoxyphenacyl triester of nitrilotriacetic acid is obtained in the form of oil (unoptimized yield: 25%).

The 500 MHz $^1$H NMR spectrum in dimethyl sulfoxide (DMSO-$d_6$) is consistent with the structure: 500 MHz $^1$HNMR (DMSO-$d_6$, δ ppm): 3.86 (9H, s), 3.88 (6H, s), 5.51 (6H, s), 7.08 (6H, dd), 7.96 (6H, dd).

Example 2

Preparation of 8-(2-nitrobenzyloxy)quinoline (compound of formula III).

1.5 g of 8-hydroxyquinoline are dissolved in 30 ml of dry methanol containing 0.7 g of sodium methoxide. After 15 minutes at ambient temperature the solution is evaporated to dryness. The product obtained is taken up in 5 ml of dimethylformamide and reevaporated. It is then dissolved in 30 ml of DMF, and 2.3 g of 2-nitrobenzyl chloride in solution in 15 ml of DMF are added to it. The solution is agitated for 45 minutes at ambient temperature. The mixture is then evaporated to dryness, and the residue obtained is dissolved in ethyl acetate. It is then washed with water, dried over sodium sulfate, and evaporated to dryness. After threefold extraction into 50 ml of petroleum ether, the insoluble material obtained is recrystallized from 50 ml of ethanol.

1.2 g of 8-(2-nitrobenzyloxy)quinoline are obtained in the form of yellow solid product (unoptimized yield 40%). Melting point: 152° C.

The $^1$H NMR spectrum in deuterochloroform ($CDCl_3$) is consistent with the structure:

500 MHz $^1$H NMR ($CDCl_3$, δ ppm): 5.83 (2H, s), 7.00 (1H, dd), 7.40 (4H, m), 7.63 (1H, td), 8.06 (1H, dd), 8.13 (1H, dd), 8.17 (1H, dd), 8.98 (1H, dd).

Example 3

Preparation of the p-methoxyphenacyl diester of N,N'-bis (2-hydroxybenzyl)ethylenediaminediacetic acid (compound of formula V).

1 g of N,N'-bis(2-hydroxybenzyl) ethylenediaminediacetic acid is dissolved in 10 ml of dimethylformamide containing 1.2 ml of triethylamine. The mixture is cooled to 0° C., and then 1 g of 2-bromo-4'-methoxyacetophenone in solution in 10 ml of dimethylformamide is added to it. The mixture is kept at 0° C. for 24 hours. The mixture is then poured onto 100 g of ice, and a three-fold extraction is carried out into 50 ml of dichloromethane. The organic phase is washed with water, dried over sodium sulfate, and then evaporated to dryness. The oil obtained is dissolved in the minimum quantity of dichloromethane, and isopropanol is added to it until the medium precipitates. The precipitate is filtered off and then is taken up twice using ethanol at reflux.

200 mg of p-methoxyphenacyl diester of N,N'-bis(2-hydroxybenzyl)ethylenediaminediacetic acid are obtained in the form of a white product (unoptimized yield: 15%). Melting point: 178° C.

The 500 MHz $^1$H NMR spectrum in DMSO is consistent with the structure:

500 MHz $^1$H NMR (DMSO-$d_6$, δ ppm): 2.80 (4H, s), 3.56 (4H, s), 3.77 (4H, s), 3.86 (6H, s), 5.47 (4H, s), 6.75 (4H, m), 7.07 (4H, dd), 7.11 (4H, dd), 7.94 (4H, dd), 9.62 (2H, s).

The following examples illustrate the cosmetic or dermatological compositions according to the invention. The quantities are given as percentage by weight, based on the total weight of the composition.

Example 4

Sun cream

| Oily phase | |
| --- | --- |
| Compound of formula (III) | 0.2% |
| Anhydrous lanolin | 1.7% |
| Isopropyl myristate | 2% |
| Cetyl alcohol | 0.15% |
| Stearic acid | 5.1% |
| Benzophenone-4 (screen) (Uvinul MS-40 marketed by BASF, aqueous solution containing 20% of active substance in water) | 25% |
| Aqueous phase | |
| Sorbitol | 4.15% |
| Carbomer (Carbopol 934 marketed by Goodrich) | 0.1% |
| Triethanolamine | 3.67% |
| Stabilizer | 0.1% |
| Water | q.s. 100% |

The preparation procedure consists in mixing the water, the carbomer, and the sorbitol and then adding a proportion of the triethanolamine, in separately preparing the oily phase by mixing the various constituents except for the screening agent, with heating (approximately 75° C.), and then introducing the oily phase into the aqueous phase with stirring and in next introducing the screening agent after having adjusted the pH of the solution containing it with the remainder of the triethanolamine.

A sun cream of off-white color is obtained, which provides good protection against the detrimental effects of ultraviolet rays.

Example 5

Hydrating care cream

| Oily phase | |
| --- | --- |
| Compound of formula (VI) | 0.1% |
| Jojoba oil | 13% |
| Stearyl alcohol | 1% |
| Stearic acid | 4% |
| Cyclopentadimethylsiloxane | 10% |
| Vitamin E | 1% |
| Polyethylene glycol stearate | 3% |
| Aqueous phase | |
| Potassium sorbate | 0.3% |
| Glycerol | 3% |
| Stabilizer | 0.05% |
| Water | q.s. 100% |

The preparation procedure consists in mixing, on the one hand, the constituents of the aqueous phase and, on the other hand, the constituents of the oily phase and in then introducing the oily phase into the aqueous phase with stirring.

A white cream is obtained which hydrates the skin well and protects it from luminous radiation.

This application is based on French patent application 94-10763 filed on Sep. 8, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A composition, comprising a chelating agent for a transition metal and a cosmetically and/or dermatologically acceptable medium, wherein said chelating agent contains a group containing at least one chelating functional group for a transition metal, blocked by a photocleavable substituent, wherein said chelating functional group is selected from the group consisting of amine, carbonyl, nitrile, oxime, carboxylic, hydroxyl, hydroxamic, alkoxy, enolic, phenolic, phenoxy, hydrazide and sulfur-containing functional groups and combinations thereof.

2. The composition of claim 1, wherein said chelating group is selected from the group consisting of hydroxypyridinones, dicarboxylic amines, o-hydroxybenzylamines and hydroxamates.

3. The composition of claim 1, wherein said photocleavable substituent is selected from the group consisting of p-methoxyphenacyl, 2-nitrobenzyl, 2-nitrobenzyloxycarbonyl, 2-nitrophenylethylene glycol, benzyloxycarbonyl, 3,5-dimethoxybenzyloxycarbonyl, α,α-dimethyl-3,5-dimethoxybenzyloxycarbonyl, 3-nitrophenyl, 3-nitrophenoxy, 3,5-dinitrophenoxy, 3-nitrophenoxycarbonyl, phenacyl, 4-methoxyphenacyl, α-methylphenacyl, 3,5-dimethoxybenzoinyl and 2,4-dinitrobenzenesulphenyl groups.

4. The composition of claim 1, wherein said photocleavable substituent is selected from the group consisting of from p-methoxyphenacyl and o-nitrobenzyl groups.

5. The composition of claim 1, wherein said transition metal has an atomic number chosen from the range running from 21 to 30.

6. The composition of claim 1, wherein said transition metal is selected from the group consisting of iron and copper.

7. The composition of claim 1, which is in the form of a salve, ointment, or cream.

8. A composition for protecting the skin, the hair, and/or the mucosa against the effects induced by luminous radiation and/or for preventing and/or combating cutaneous photoaging, comprising a chelating agent for a transition metal and a cosmetically and/or dermatologically acceptable medium, wherein said chelating agent contains a group containing at least one chelating functional group for a transition metal, blocked by a photocleavable substituent, wherein the composition is in the form of a salve, ointment, or cream.

9. A method for chelating a transition metal comprising applying a compound containing a group containing at least one chelating functional group for a transition metal blocked by at least one photocleavable substituent to an environment which contains a transition metal and is subject to exposure to ultraviolet radiation, wherein said chelating functional group is selected from the group consisting of amine, carbonyl, nitrile, oxime, carboxylic, hydroxyl, hydroxamic, alkoxy, enolic, phenolic, phenoxy, hydrazide and sulfur-containing functional groups and combinations thereof.

10. The method of claim 9, wherein said chelating group is selected from the group consisting of hydroxypyridinones, dicarboxylic amines, o-hydroxybenzylamines and hydroxamates.

11. The method of claim 9, wherein said photocleavable substituent is selected from the group consisting of p-methoxyphenacyl, 2-nitrobenzyl, 2-nitrobenzyloxycarbonyl, 2-nitrophenylethylene glycol, benzyloxycarbonyl, 3,5-dimethoxybenzyloxycarbonyl, α,α-dimethyl-3,5-dimethoxybenzyloxycarbonyl, 3-nitrophenyl, 3-nitrophenoxy, 3,5-dinitrophenoxy, 3-nitrophenoxycarbonyl, phenacyl, 4-methoxyphenacyl, α-methylphenacyl, 3,5-dimethoxybenzoinyl and 2,4-dinitrobenzenesulphenyl groups.

12. The method of claim 9, wherein said photocleavable substituent is selected from the group consisting of from p-methoxyphenacyl and o-nitrobenzyl groups.

13. The method of claim 9, wherein said transition metal has an atomic number chosen from the range running from 21 to 30.

14. The method of claim 9, wherein said transition metal is selected from the group consisting of iron and copper.

15. A method for protecting the skin, the hair, and/or the mucosa against the effects induced by luminous radiation and/or for preventing and/or combating cutaneous photoaging, comprising applying to the skin, the hair, or the mucosa a chelating agent for a transition metal, wherein said chelating agent contains a group containing at least one chelating functional group for a transition metal, blocked by a photocleavable substituent wherein said chelating functional group is selected from the group consisting of amine, carbonyl, nitrile, oxime, carboxylic, hydroxyl, hydroxamic, alkoxy, enolic, phenolic, phenoxy, hydrazide and sulfur-containing functional groups and combinations thereof.

* * * * *